US00PP36404P2

(12) United States Plant Patent
Bridgen et al.

(10) Patent No.: US PP36,404 P2
(45) Date of Patent: Jan. 21, 2025

(54) ***ALSTROEMERIA* PLANT NAMED 'CORAL CHAOS'**

(50) Latin Name: ***Alstroemeria* hybrid L.**
Varietal Denomination: Coral Chaos

(71) Applicant: Cornell University, Ithaca, NY (US)

(72) Inventors: Mark P. Bridgen, Southold, NY (US); Ockert F. Greyvenstein, Geneva, IL (US); Elizabeth K. Bresky, Twinsburg, OH (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 18/421,839

(22) Filed: Jan. 24, 2024

(51) Int. Cl.
*A01H 5/02* (2018.01)
*A01H 6/56* (2018.01)

(52) U.S. Cl.
USPC ..... Plt./309
CPC ..... *A01H 6/564* (2018.05)

(58) Field of Classification Search
USPC ..... Plt./309
CPC ..... A01H 5/02
See application file for complete search history.

(56) References Cited

U.S. PATENT DOCUMENTS

PP10,030 P 9/1997 Bridgen et al.
PP18,183 P3 11/2007 Bridgen
PP22,701 P3 5/2012 Bridgen

OTHER PUBLICATIONS https://www.greenhousemag.com/news/cornell-university-introduces-new-alstroemeria-coral-chaos/; Nov. 17, 2023; 2 pages.*
https://www.greenhousegrower.com/crops/cornell-university-introduces-new-alstroemeria-for-usda-zone-5/; Nov. 20, 2023; 4 pages.*
https://www.instagram.com/ccesuffolk/p/C0m3DAxScv8/?next=%2Fp%2FB44uqdjIQHF%2F&hl=hi; Dec. 8, 2023; 1 page.*
https://gpnmag.com/news/cornell-university-introduces-new-winter-hardy-alstroemeria/; Nov. 15, 2023; 3 pages.*
https://www.gardencentermag.com/news/cornell-university-introduces-new-alstroemeria-coral-chaos/; Nov. 17, 2023; 2 pages.*

* cited by examiner

*Primary Examiner* — Kent L Bell
(74) *Attorney, Agent, or Firm* — Foley & Lardner LLP

(57) ABSTRACT

An *Alstroemeria* plant particularly distinguished with vibrant coral colored flowers. The flowers on this plant have coral tepals with intense yellow highlights and little flecks of brown on the base of the inner tepals. Has a good longevity as a cut flower, continuous flowering from summer through fall, and winter-hardy from USDA zone 5 as described.

2 Drawing Sheets

ACKNOWLEDGEMENT OF FEDERAL RESEARCH SUPPORT

This invention was made, at least in part, with government support under Hatch Funding from the U.S. Department of Agriculture, Project Number NYS-145321, in cooperation with Cornell University's State Agricultural Experiment Stations. Accordingly, the United States government has certain rights in this invention.

Latin name of the genus and species of the plant claimed: *Alstroemeria* hybrid L.

Variety denomination: 'Coral Chaos'.

BACKGROUND OF THE INVENTION

The present invention comprises a new and distinct variety of *Alstroemeria*, botanically known as *Alstroemeria* hybrid L., and hereinafter referred to by the variety name 'Coral Chaos'. 'Coral Chaos' originated from a hybridization made in May 2004 in Riverhead, N.Y. The female parent was an un-named individual plant of *Alstroemeria aurea* (unpatented), while the male parent was a proprietary *Alstroemeria* plant named 'Coral 1' (unpatented). The plant was asexually propagated by rhizome division in Riverhead, New York in May of 2004. The use of R.H.S. throughout the application is in reference to The Royal Horticultural Society Colour Chart (2001).

BRIEF SUMMARY OF THE INVENTION

'Coral Chaos' is a vigorous-growing Inca Lily with vibrant coral colors. The large 2-inch flowers on this plant have coral tepals on the outside with intense yellow highlights and little flecks of brown on the base of the inner tepals. Strong, upright flower stems are produced from underground rhizomes and grow 20-28 inches tall in full sun. The flowers make excellent fresh cut flowers that can thrive for up to two weeks in a vase.

This Inca Lily was hybridized by using species that are native to Chile. In states with cool to mild summers they bloom continuously throughout the season from May until frost. In warmer states, Inca Lilies will flower in the spring and early summer until it gets hot, and then rebloom in the fall when the temperatures get cooler. 'Coral Chaos' is hardy to the U.S. Department of Agriculture zone 5 (2023 plant hardiness map) when grown with good drainage.

The following are the most outstanding and distinguishing characteristics of this new variety when grown under normal commercial practices in a glass greenhouse or outdoor field in Riverhead, N.Y., which in combination distinguishes this *Alstroemeria* plant as a new and distinct variety:

1. Vibrant coral-colored flowers;
2. Has good longevity as a cut flower;

3. Continuous flowering from the beginning of summer until the first hard freeze in fall.
4. Winter-hardy from USDA zone 5.

COMPARISON WITH PARENTAL AND COMMERCIAL CULTIVARS

The female parent, *Alstroemeria aurea* (unpatented plant), is a species that is native to southern Chile and it differs from 'Coral Chaos' by having yellow to orange flowers and by flowering only in the Spring and early Summer whereas 'Coral Chaos' has coral colored flowers and flowers continuously from the beginning of summer until the first hard freeze in fall.

The male parent, 'Coral 1' (unpatented), has smaller flowers than 'Coral Chaos' with a different shade of orange and is not as floriferous as 'Coral Chaos'. In addition, 'Coral 1' is not winter hardy to USDA zone 5, whereas 'Coral Chaos' is winter hardy down to USDA zone 5.

'Coral Chaos' differs from the commercial *Alstroemeria* cultivar 'Sweet Laura' (U.S. Plant Pat. No. 10,030), by having coral flowers that lack fragrance, whereas 'Sweet Laura' has yellow flowers that are fragrant. Both cultivars are winter hardy to USDA zone 5.

'Coral Chaos' differs from 'Mauve Majesty' (U.S. Plant Pat. No. 18,183) and 'Tangerine Tango' (U.S. Plant Pat. No. 22,701) by having larger flowers than those two cultivars and significantly different flower colors.

BRIEF DESCRIPTION OF THE PHOTOGRAPHS

This new *Alstroemeria* plant is illustrated by the accompanying photographs which show blooms and foliage of the plant. The colors shown are as true as can be reasonably obtained by conventional photographic procedures. The plants in the photographs are approximately one year old.

DETAILED BOTANICAL DESCRIPTION

Figure 1:
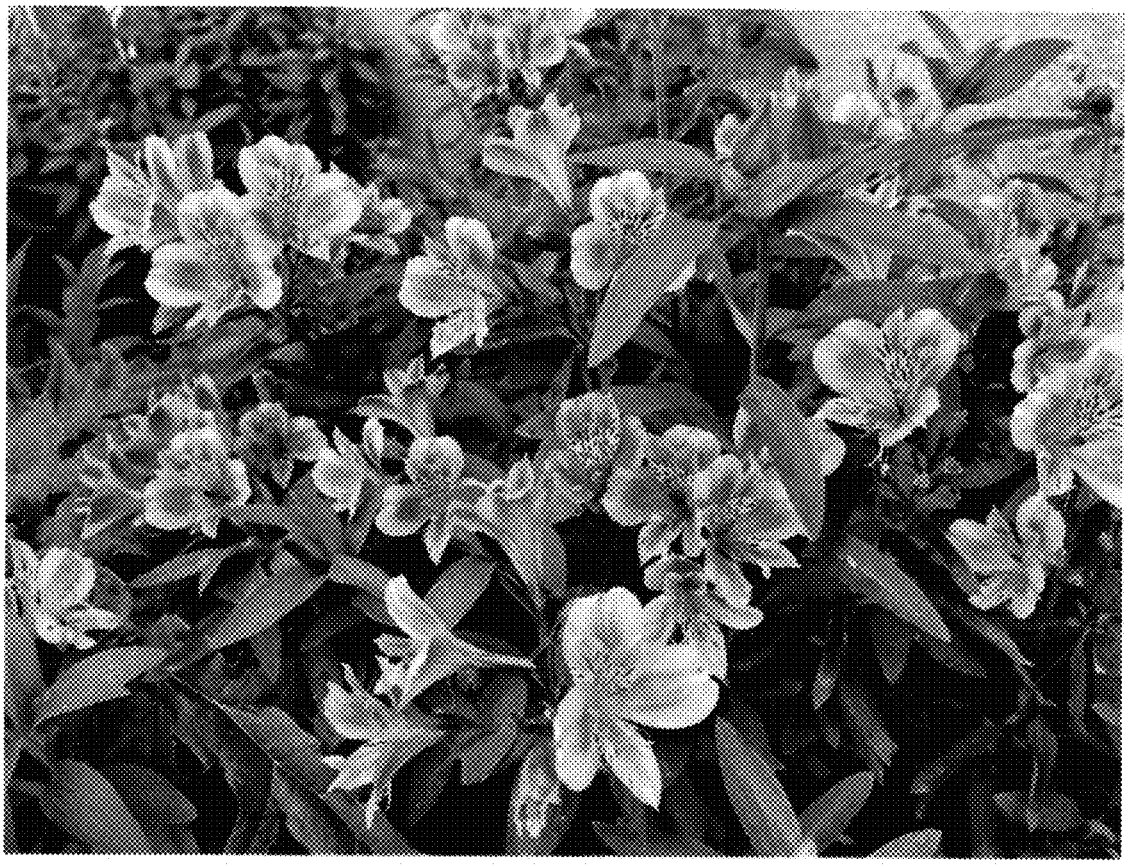
FIG. 1 shows the overall plant habit, including mature inflorescences, flower buds, and leaves.
Figure 2:
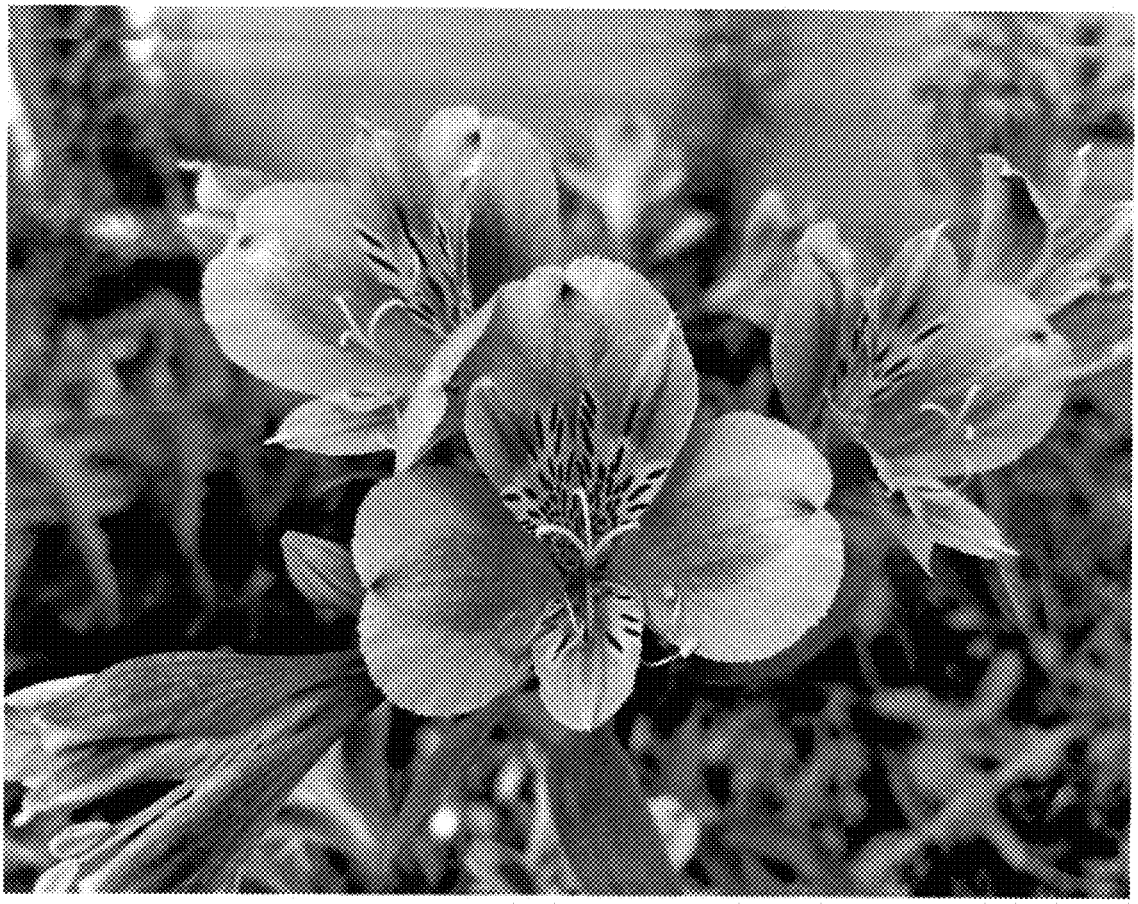
FIG. 2 shows a close-up of a mature inflorescence.

Classification:
- *Botanical.*—*Alstroemeria* hybrid L.
- *Common name.*—*Alstroemeria*, Lily-of-the-Incas; Inca Lily; Peruvian Lily.

Plant:
- *Form.*—Herbaceous plant arising from an underground rhizome.
- *Habit.*—Upright and vigorous.
- *Plant height.*—66-92 cm (26"-36").
- *Plant width (spread).*—92-100 cm (36"-39").
- *Flowering habit.*—Continuous flowering from the beginning of summer until the first hard freeze in fall.
- *Time to produce a finished flowering plant.*—If a clump is divided in the spring or early summer, it will resume flowering within 4-6 weeks.

Flowering stems:
- *Color.*—RHS 137A or RHS 137C.
- *General description.*—Long, strong, and upright growing floral stems.
- *Stem strength.*—Strong.

Size:
- *Length.*—66-91 cm (26"-36").
- *Diameter.*—1-2 cm (0.4"-0.8").
- *Internode length.*—Not applicable.
- *Texture.*—Glabrous.

Leaves:
- *Arrangement.*—Simple, linear, resupinate leaves with parallel venation that are arranged alternately.
- *Shape.*—Elongated elliptic with extended bases.
- *Apex.*—Broadly acuminate apices.
- *Base.*—Narrowed and resupinate.
- *Margin.*—Entire.
- *Color, mature leaf.*—Upper surface: RHS 137A or RHS 137C. Lower surface: RHS 137A or RHS 137C.
- *Size.*—Length: 6.5-10 cm (2.5"-4"). Width: 1.5-2.2 cm (0.6"-0.87").
- *Texture.*—Glabrous upper leaf surface.
- *Venation.*—Parallel. Upper surface: RHS 137A or RHS 137C. Lower surface: RHS 137A or RHS 137C.
- *Pubescence.*—None.
- *Petiole.*—None (sessile leaves).

Flowers:
- *Inflorescence type.*—A terminal bracted umbel of cymes.
- *Flowering season.*—Early summer through early Fall.
- *Lastingness of individual flowers on the plant.*—15-21 days.
- *Post harvest life of cut flowers.*—10-14 days.
- *Color.*—RHS 37B on outside margins of tepals to RHS 39A on inside.
- *Flower width.*—Approximately 5-6 cm at the open end.
- *Flower depth.*—5 cm from tip to receptacle (2").
- *Flower shape.*—Tubular.
- *Fragrance.*—None.
- *Number of flowers per plant.*—Everblooming; varies with size of plant; 30-50/3 months.
- *Number of florets per umbel.*—Typical: 12. Range: 8-12.
- *Peduncle.*—Length: 2-6 cm. Diameter: Approximately 0.2-0.4 cm. Surface Texture: Glabrous and Smooth. Color: RHS 137A (Green) or RHS137C (Green).
- *Flower buds.*—Color: RHS 146C to RHS 137D. Shape: Pear-shaped becoming long and more pointed just before opening. Length: Approximately 2.5 to 4 cm before opening. Diameter: Approximately 0.9 to 1 cm before opening.
- *Tepals.*—Arrangement: Two concentric circles of three tepals each. Shape: Tubular/spatulate to oblanceolate-spatulate. Length: 3.7-4.2 cm. Width: Approximately 5-6 cm at the tip. The base (proximal) portions of inner tepals are RHS 12B (yellow) sprinkled with short, narrow, flecks approximately 2 to 7 mm in length which are colored RHS 183A (Greyed-purple). The apices of the three outer tepals are RHS 139C to 137C (Green).
- *Apex.*—Emarginate to mucronate to apiculate apices.
- *Texture.*—Glabrous and smooth. Upper surface: Glabrous and smooth. Lower surface: Not as glabrous as upper surface and not as smooth.
- *Color.*—See flower colors description above. Upper and lower tepal surfaces are the same.

Reproductive organs:
- *Pistils.*—Stigma is tripartite when ripe and RHS 37B.
- *Quantity.*—1. Style length: 2.5-4.0 cm. Style color: RHS 37B at distal end fading to RHS 138D at base (proximal end).
- *Stamens.*—Quantity: 4-6. Anther length: 7.0-8.0 mm. Anther width: 2.0 mm. Anther color: RHS 154C.

Filaments length: Approximately 3.0-4.0 cm. Pollen: Flowers are sterile; no pollen.

Seeds: No seed set; empty ovaries are produced.

Disease and insect resistance: Because this plant is sterile, there is no viable pollen and thrips are less likely to attack. Plants have few disease problems.

We claim:

1. A new and distinct *Alstroemeria* plant named 'Coral Chaos', as herein described and illustrated by the characteristics set forth above.

* * * * *